(12) United States Patent
Vandenbroek et al.

(10) Patent No.: US 8,475,473 B2
(45) Date of Patent: Jul. 2, 2013

(54) CONVERTIBLE SURGICAL CLIP APPLIER SYSTEM

(75) Inventors: Frans Vandenbroek, Rancho Santa Margarita, CA (US); Luong Nguyen, Irvine, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1634 days.

(21) Appl. No.: 10/815,149

(22) Filed: Mar. 30, 2004

(65) Prior Publication Data

US 2005/0222588 A1   Oct. 6, 2005

(51) Int. Cl.
 *A61B 17/10* (2006.01)
(52) U.S. Cl.
 USPC .......................................... 606/142
(58) Field of Classification Search
 USPC ................. 606/139, 142, 144, 151, 157, 143, 606/158; 227/175.1
 See application file for complete search history.

(56) References Cited

U.S. PATENT DOCUMENTS

| | | | |
|---|---|---|---|
| 3,777,538 A * | 12/1973 | Weatherly et al. | 72/409.01 |
| 3,827,277 A * | 8/1974 | Weston | 72/409.01 |
| 4,226,242 A | 10/1980 | Jarvik | |
| 4,296,751 A | 10/1981 | Blake, III | |
| 4,425,915 A | 1/1984 | Ivanov | |
| 4,427,008 A | 1/1984 | Transue | |
| 4,430,997 A | 2/1984 | DiGiovanni | |
| 4,448,193 A | 5/1984 | Ivanov | |
| 4,500,024 A | 2/1985 | DiGiovanni | |
| 4,712,549 A | 12/1987 | Peters | |
| 5,015,249 A * | 5/1991 | Nakao et al. | 606/142 |
| 5,084,057 A | 1/1992 | Green | |
| 5,163,945 A * | 11/1992 | Ortiz et al. | 606/142 |
| 5,174,487 A | 12/1992 | Rothfuss | |

(Continued)

FOREIGN PATENT DOCUMENTS

| | | |
|---|---|---|
| EP | 0 793 944 A1 | 9/1997 |
| WO | WO 02/28268 A | 4/2002 |
| WO | WO 2004/008944 A | 1/2004 |

OTHER PUBLICATIONS

Co-Pending U.S. Appl. No. 11/021,852, filed Dec. 23, 2004, Title: Surgical Instrument With Improved Handle Assembly.

(Continued)

*Primary Examiner* — Thomas McEvoy
(74) *Attorney, Agent, or Firm* — John F. Heal; Pui Tong Ho; Richard L. Myers

(57) ABSTRACT

A surgical clip applier includes a handle assembly, a first clip assembly, and a second clip assembly. The first clip assembly is adapted to receive only a single clip while the second clip assembly is adapted to receive multiple clips. The handle assembly is sized and configured to receive the first clip assembly or the second clip assembly. A jaw assembly includes a pair of jaws each with an elongate support arm, and a bridge holding the jaws in an aligned relationship. A housing has a fixed relationship with the bridge while permitting movement of the jaws between an open and a closed state. A coupling attaches the housing to the handle assembly. An associated method of operation includes the step of removing one of the single clip jaw assembly and the multiple clip-jaw assembly, disposing of the one jaw assembly while mounting the other jaw assembly on the handle.

14 Claims, 7 Drawing Sheets

U.S. PATENT DOCUMENTS

| | | | |
|---|---|---|---|
| 5,246,156 A | | 9/1993 | Rothfuss |
| 5,282,812 A | | 2/1994 | Suarez, Jr. et al. |
| 5,333,772 A | | 8/1994 | Rothfuss |
| 5,354,304 A | * | 10/1994 | Allen et al. .................... 606/142 |
| 5,429,609 A | | 7/1995 | Yoon |
| 5,431,668 A | | 7/1995 | Burbank, III |
| 5,470,010 A | | 11/1995 | Rothfuss |
| 5,527,318 A | | 6/1996 | McGarry |
| 5,551,622 A | | 9/1996 | Yoon |
| 5,560,532 A | | 10/1996 | DeFonzo |
| 5,651,491 A | | 7/1997 | Heaton |
| 5,702,048 A | * | 12/1997 | Eberlin ...................... 227/177.1 |
| 5,762,256 A | | 6/1998 | Mastri |
| 5,772,673 A | | 6/1998 | Cuny |
| 5,925,064 A | * | 7/1999 | Meyers et al. ................. 606/205 |
| 5,938,667 A | * | 8/1999 | Peyser et al. .................. 606/142 |
| 5,972,003 A | | 10/1999 | Rousseau |
| 6,032,849 A | | 3/2000 | Mastri |
| 6,109,500 A | | 8/2000 | Alli |
| 6,238,373 B1 | | 5/2001 | De la Torre et al. |
| 6,446,854 B1 | | 9/2002 | Remiszewski |
| 6,599,298 B1 | * | 7/2003 | Forster et al. ................. 606/139 |
| 6,896,683 B1 | * | 5/2005 | Gadberry et al. .............. 606/142 |
| 7,028,878 B2 | * | 4/2006 | Bauer ......................... 227/175.1 |
| 2008/0234705 A1 | * | 9/2008 | Cropper et al. ............... 606/157 |

OTHER PUBLICATIONS

Co-Pending U.S. Appl. No. 10/381,970, filed Mar. 5, 2004. Title: Multiple Clip Applier Apparatus and Method.

Co-Pending U.S. Appl. No. 11/039,188, filed Jan. 19, 2005. Title: Single Fire Vascular Clip Applier With Disposable Jaw.

Co-Pending U.S. Appl. No. 10/518,436, filed Dec. 16, 2004. Title: Clip Applier Cartridge With Internal Ratchet.

Co-Pending U.S. Patent Appl. No. 11/536,467, filed Sep. 28, 2006. Title: Manually Actuated Surgical Clip Applier.

The International Search Report and the Written Opinion of the International Searching Authority for PCT application No. PCT/US2005/008319.

* cited by examiner

CONVERTIBLE SURGICAL CLIP APPLIER SYSTEM

BACKGROUND OF THE INVENTION

1. Field of the Invention

This invention relates generally to surgical clip appliers and more specifically to clip appliers having a handle assembly in a scissors configuration.

2. Discussion of the Relevant Art

Surgical clips are commonly used to occlude body conduit such as blood vessels. In the past, clip appliers have been used to place the clip in an open state over the blood vessel and then to crimp the clip to a closed state thereby pinching and holding the vessel in an occluded configuration.

In some cases, the clip appliers are adapted to work with only one clip at a time. A clip is manually placed between jaws of the clip applier and crimped onto the blood vessel before a second clip is manually loaded into the applier. Such devices are commonly referred to as single-fire clip appliers.

By comparison, multiple clips have been housed in a clip cartridge, which is then mounted on a handle assembly. Operation of the handle assembly causes one of the clips in the cartridge to be automatically loaded into the jaws for ultimate application at the operative site. With such a system, multiple clips can be applied at the site by mere operation of the handle assembly and the cartridge. Such a system is disclosed and claimed in Applicant's co-pending patent application Ser. No. 10/381,970 filed on Mar. 28, 2003 and entitled "Multiple Clip Applier Apparatus and Method", which is fully incorporated herein by reference. Such clip appliers are commonly referred to as multiple-fire clip appliers.

In the past, each single fire clip applier and each multiple-fire clip applier was provided with its own handle assembly. Often both types of appliers were required for a particular surgical procedure, so that multiple instruments were needed. This not only increased the cost of a given procedure but also consumed additional space among the instruments in the operating room.

Single-fire clip appliers have not been formed with cartridges. Rather, the handle assembly has been provided with the jaws necessary to receive and crimp the clip. In these single-fire devices, the instrument is formed entirely of metal and has been designed for repeated use and sterilization, for example, in an autoclave. It is this autoclaving procedure which has often resulted in bending or otherwise damaging the jaws, ultimately resulting in clip misalignment and a general inability to receive and apply the clip.

SUMMARY OF THE INVENTION

In accordance with the present invention, a clip applier system includes a single handle assembly that is adapted to receive either a single-fire cartridge or a multiple-fire cartridge. The critical jaws are included in the cartridges rather than the handle assembly, and are intended to be disposable. Only the handle assembly, which is free of critical components such as the jaw, is adapted for autoclaving. With this system, only a single handle assembly need be purchased and provided in the operating room. The two types of cartridges can be alternatively mounted on the handle assembly to provide either the single-fire or the multiple-fire capability. In both cases, the disposable cartridges are provided with jaws so each new cartridge offers a new set of jaws for each procedure.

In one aspect, the invention includes a surgical clip applier having a handle assembly disposed in a first plane, and first and second clip assemblies disposed in second and third planes, respectively. The first clip assembly is adapted to receive only a single clip in a first operative position, wherein the second plane is generally parallel to the first plane. The second clip assembly is adapted to receive multiple clips in a second operative position, wherein the third plane is generally parallel to the first plane. The handle assembly is sized and configured to receive alternatively the first clip assembly in the first operative position and the second clip assembly in the second operative position.

In another aspect, the invention includes a jaw assembly adapted for use with a handle assembly in a surgical clip applier. The jaw assembly includes a pair of jaws adapted to receive a surgical clip, the jaws being movable between an open state and a closed state. A pair of elongate support arms are adapted to support an associated one of the jaws between the open state and the closed state of the jaws. A bridge disposed between the support arms holds the jaw in an aligned relationship between the open and closed states. A housing disposed over at least the bridge, has a generally fixed relationship with the bridge while permitting movement of the jaws between the open and the closed state. A coupling included in the housing is adapted for attaching the housing to the handle assembly.

A method of operating a surgical clip applier is included in another aspect of the invention. In this case, the clip applier includes a handle, a single clip jaw assembly, and a multiple clip jaw assembly. The method includes the steps of removing one of the single clip jaw assembly and the multiple clip jaw assembly, disposing of the one jaw assembly and mounting the other jaw assembly on the handle in an overlying operative relationship with the handle.

DESCRIPTION OF PREFERRED EMBODIMENTS AND BEST MODE OF THE INVENTION

Figure 1:
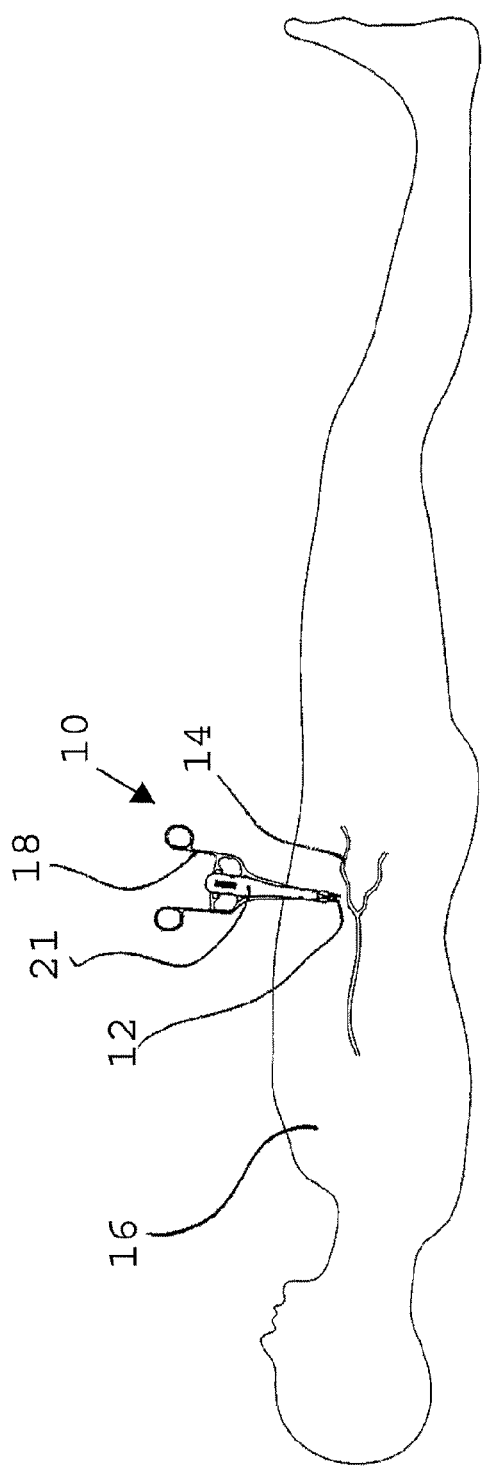
FIG. 1 is a schematic view of a patient involved in a surgical procedure, and a clip applier of the present invention operatively positioning a clip on a vein of the patient.

The surgical clip applier is illustrated in FIG. 1 and designated by the reference numeral 10. In this view, the clip applier 10 is operatively disposed to apply a clip 12 to a blood vessel 14 in the leg of a patient 16. The clip applier 10 includes a reusable handle assembly 18 and a disposable jaw assembly 21.

Figure 2:
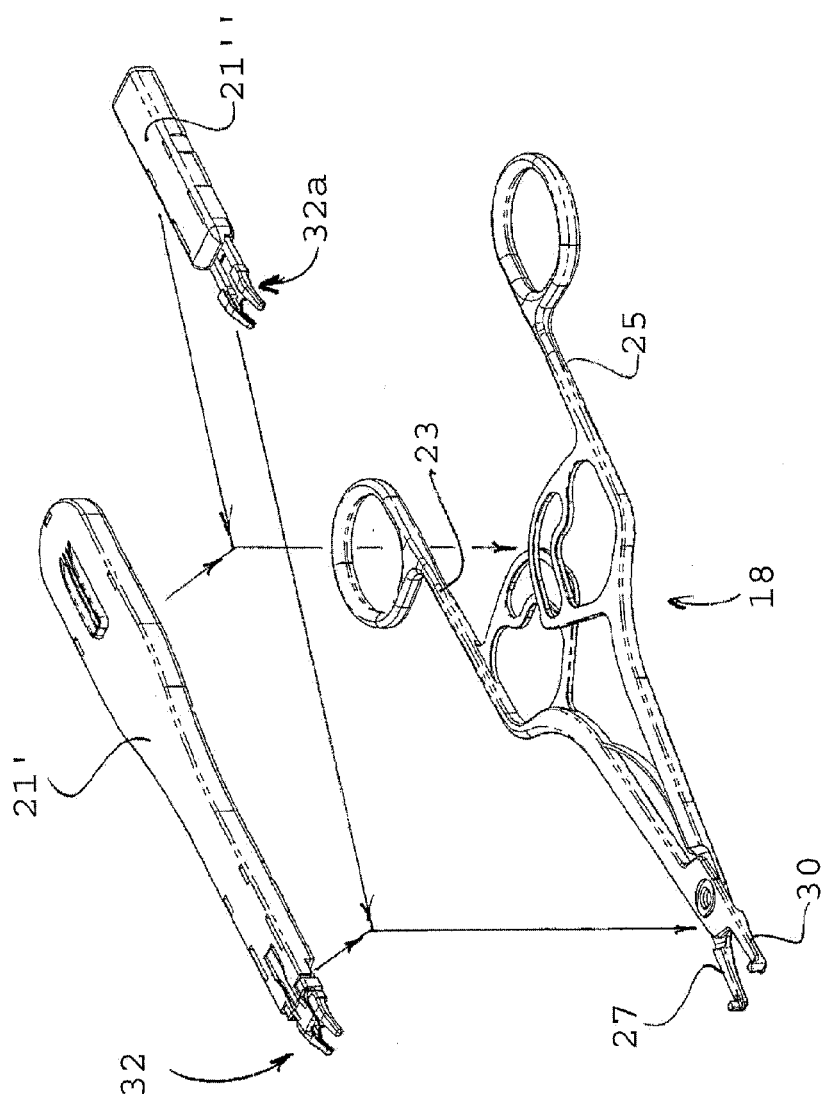
FIG. 2 is a schematic perspective view illustrating a non-disposable handle assembly adapted for alternative use with a disposable multiple-clip cartridge and a disposable single-clip cartridge.

As best illustrated in the embodiment of FIG. 2, the handle assembly 18 will typically include a pair of handles 23 and 25 which control a pair of arms 27 and 30 in a scissors configuration. The jaw assembly 21 can be provided in various forms to facilitate a particular operative procedure. For example, the jaw assembly 21 may be provided in the form of a multiple-fire clip assembly 21' or a single-fire clip assembly 21". These two assemblies 21' and 21" can be alternatively attached to the handle assembly 18 as illustrated in FIG. 2.

An advantage of this convertibility is appreciated when one recognizes that the handle assembly 18 can be made reusable while the jaw assemblies 21' and 21" can be made disposable. Importantly, each of the jaw assemblies 21' and 21" can be provided with a new jaw component 32, having the critical jaw alignment. Since the jaw assemblies 21' and 21" are intended to be disposable, it follows that a new jaw component 32 is provided with each new use of the clip applier 10. In this manner the critical jaw component 32 can be isolated from the damaging environment of an autoclave. The handle assembly 18 on the other hand does not include the critical jaw component 32 and accordingly can be sterilized in an autoclave without concern.

Figure 3:
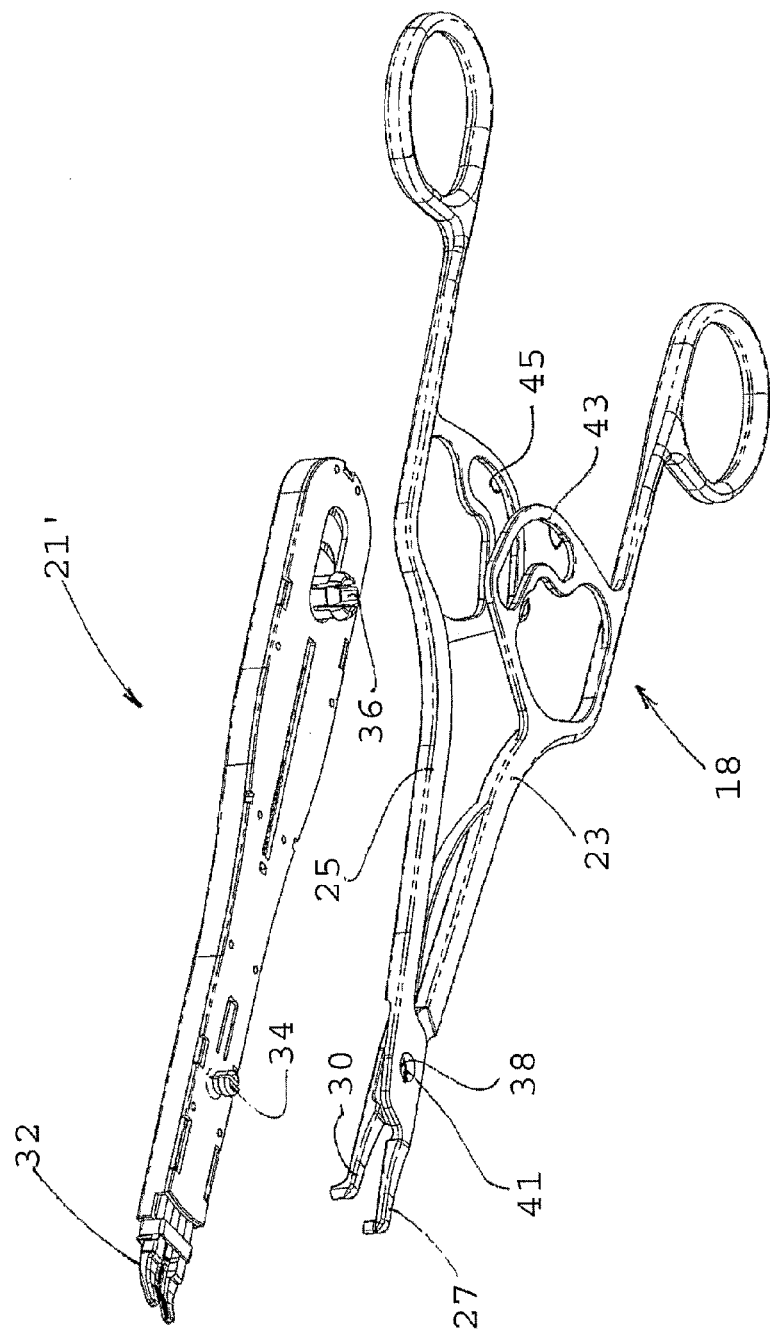
FIG. 3 is a bottom perspective assembled view showing the multi-clip cartridge positioned for attachment to the handle assembly.

In the assembly view of FIG. 3, the handle assembly 18 is illustrated along with the jaw assembly 21'. This particular assembly 21' functions as a multiple-fire clip cartridge in the manner disclosed and claimed in applicant's co-pending application Ser. No. 10/381,970 filed on Mar. 28, 2003 and entitled "Multiple Clip Applier Apparatus and Method". This assembly 21' includes the critical jaw component 32 as well as a mounting stub 34 and an operating stub 36. Movement of the operating stub 36 relative to the mounting stub 34 operates to load a new clip into the jaws of the component 32.

Figure 4:
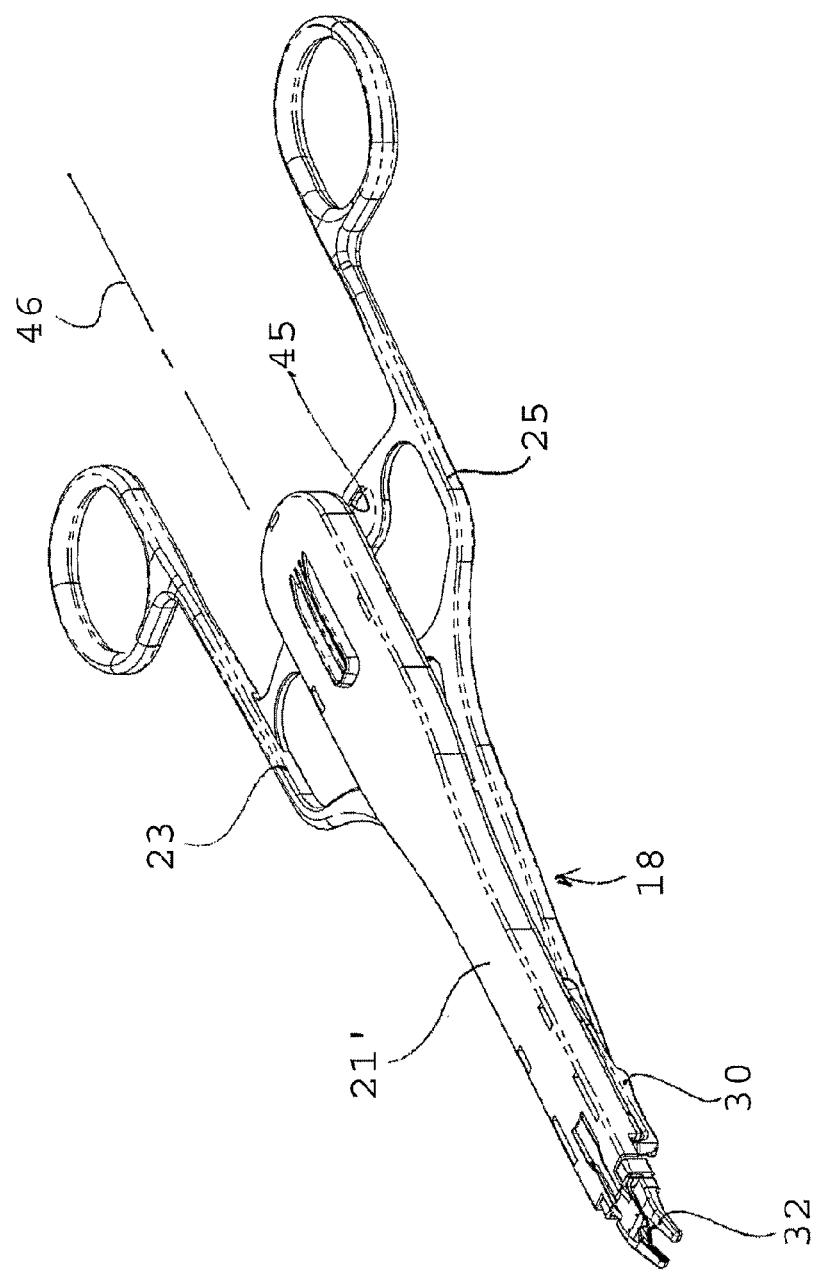
FIG. 4 is a top perspective view illustrating the multiple-fire cartridge attached to the handle assembly.

This jaw assembly 21' is sized and configured for operation with the handle assembly 18 which includes the handles 23 and 25 as well as the arms 27 and 30. A special hinge 38 defines a pivot point for the scissors configuration and includes an aperture 41 which is formed at the pivot point and sized to removably receive the mounting stub 34. The handles 23 and 25 are configured to define intersecting slots 43 and 45, respectively, which in turn are configured to receive the operating stub 36. When the handles 23 and 25 are moved in a scissors manner, the slots 43 and 45 define a point of intersection which is moveable along an axis 46 of the handle assembly 18. With the operating stub 36 disposed in this moving point of intersection, the stub 36 is also moved axially to load a new clip into the jaw component 32. With the stub 34 mounted along the axis 46 and the stub 36 moveable along the axis 46, the jaw assembly 21' is also maintained along the axis 46 of the handle assembly 18 as illustrated in the assembled view of FIG. 4.

Figure 5:
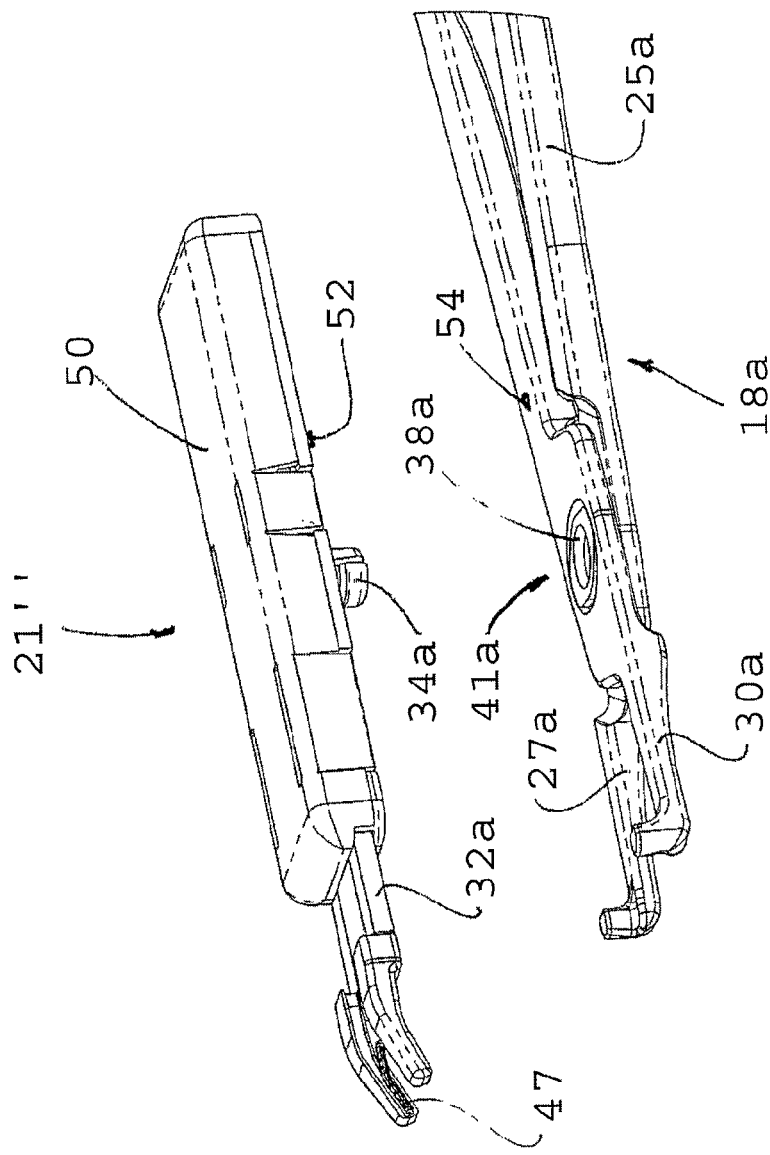
FIG. 5 is an assembled perspective view illustrating the single-fire cartridge positioned for attachment to the handle assembly.
Figure 6:
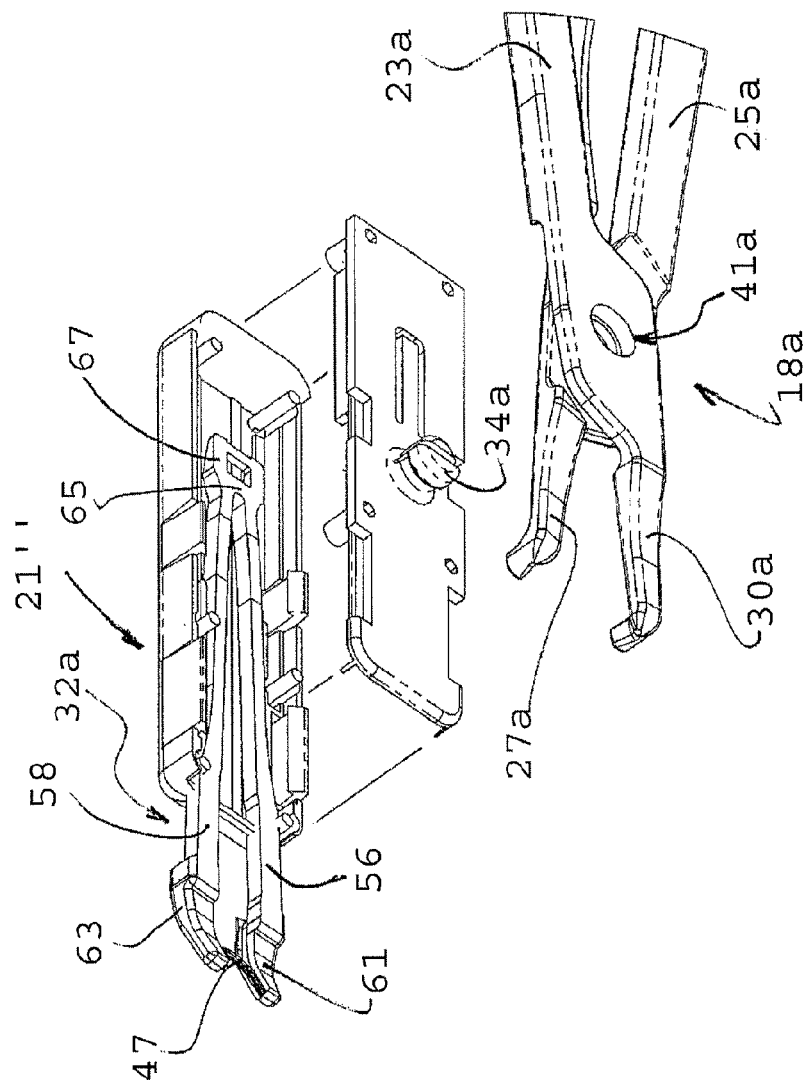
FIG. 6 is a bottom perspective view of the single-fire cartridge positioned for attachment to the handle assembly.

The single-fire clip assembly 21" and handle assembly 18 are illustrated in the top assembly prospective view of FIG. 5. In this embodiment, elements of similar structure are designated with the same reference numeral followed by the lower case letter "a." A bottom perspective view of the cartridge 21" is illustrated with a handle assembly 18a in FIG. 6. From this view it can be seen that in a preferred embodiment, the jaw assembly 21" can be formed with the jaw component 32a having a pair of legs 56 and 58 which extend to respective jaws 61 and 63 that hold the clip 47. Within the housing 50, the legs 56 and 58 are joined by a bridge 65 and an extension 67. This provides the jaw component 32a with the general configuration of a tuning fork.

The handle assembly 18a, in this case, is preferably exactly the same as that illustrated in the previous embodiment. This enables the handle assembly 18a to be reusable and reconfigured for combination with the alternative jaw assemblies 21' and 21". Thus, the handle assembly 18a in FIG. 5 includes the handles 23a and 25a as well as the arms 27a and 30a which scissor at the hinge 38a. It is this hinge 38a which is provided with the mounting hole or aperture 41a.

Also illustrated in FIG. 5 is a top perspective view of the jaw assembly 21". This jaw assembly 21" functions by loading the jaw component 32a with a clip 47 exteriorly of the jaw assembly 21'. In this embodiment, the jaw component 32a is provided with housing 50 which includes the mounting stub 34a and may also include at least one second mounting stub 52.

In order to initially form the combination of the handle assembly 18 and cartridge 21", the mounting stub 34 is inserted into the aperture 41 in the hinge 48 of the handle assembly 18. With this single mounting stub 34, the jaw component 32a will be free to float between the arms 27 and 30 of the handle assembly. If this is objectionable, the second mounting stub 52 may be provided for insertion into a second aperture 54 in the handle assembly 18.

The extension 67 has no function in this embodiment of the jaw assembly 21'. However, in the interest of maintaining the jaw component 32a with the same configuration in both embodiments of the jaw assembly 21, this extension 67 which has a function in the jaw assembly 21' is retained in the jaw assembly 21".

Figure 7:
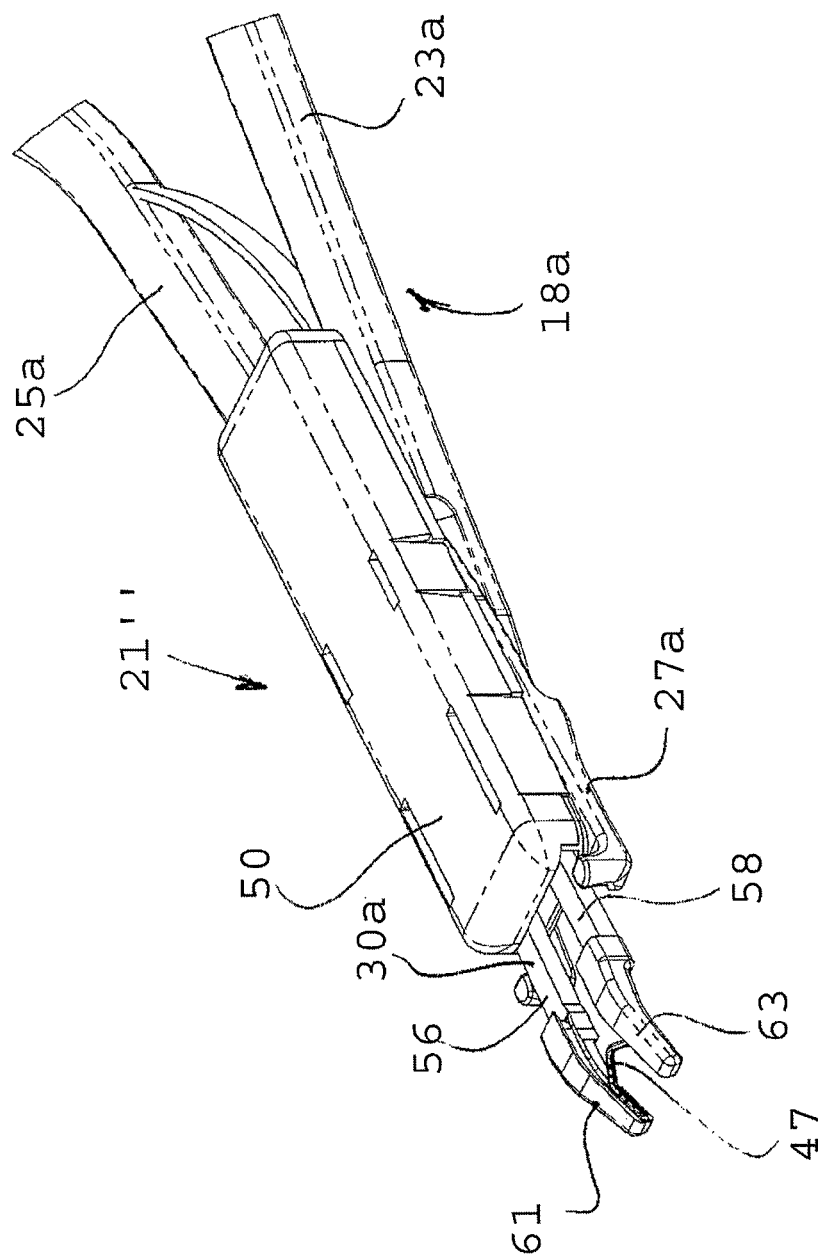
FIG. 7 is a top perspective view illustrating the single-fire cartridge operatively combined with the handle assembly.

A final assembled view of the combination is illustrated in FIG. 7. Here it can be seen that the jaw assembly 21" is mounted in an operative disposition relative to the handle assembly 18a. As is the case with the jaw assembly 21', the similar jaw component 32a is positioned with its legs 56 and 58 disposed adjacent to the arms 27a and 30a, respectively.

In operating this embodiment of the clip applier 10, the clip 47 is retrieved from a separate tray of clips (not shown) to load the jaws 61 and 63. This point in the process is illustrated in FIG. 7. After the clip 47 has been loaded, the clip applier 10 can be moved to the operative site as illustrated in FIG. 1 and the handle assembly operated to crimp the clip 47 over the vessel 14.

Although this inventive combination has been disclosed with reference to only two embodiments of the jaw assembly 21, it will be apparent that other jaw assemblies can be similarly combined with the reusable handle assembly 18. With that appreciation, one will realize that the current invention is not limited to merely the embodiments illustrated and disclosed, but other embodiments will be apparent to those of ordinary skill in the art. Accordingly, the scope of protection should not be ascertained merely with reference to the drawings and disclosure but more importantly with reference to the following claims.

The invention claimed is:

1. A single clip jaw assembly, comprising:
    a handle assembly having at least one handle and defining a central longitudinal axis wherein said handle assembly has a scissor configuration and is capable of grasping an object; and
    a single cartridge comprising:
        a pair of jaws adapted to receive a surgical clip, the jaws being movable between an open state and a closed state;
        a pair of elongate support arms each adapted to support an associated one of the jaws between the open state of the jaws and the closed state of the jaws;
        a bridge disposed between the support arms hold the jaws in an aligned relationship between the open state and the closed state;
        a housing disposed over at least the bridge, the housing having a generally fixed relationship with the bridge while permitting movement of the jaws between the open state and the closed state, and the housing having no automatic clip loading mechanism housed therein; and a coupling included on the housing, the coupling being adapted for removably attaching the housing to the handle assembly to an operative disposition such that the housing is rotationally fixed with respect to the at least one handle of the handle assembly about the central longitudinal axis and such that actuation of the at least one handle moves the jaws between the open state and the closed state, wherein the coupling comprises a first mounting stub configured to be received by a first mounting aperture of the handle assembly and a second mounting stub configured to be received by a second mounting aperture of the handle assembly, and;

wherein the jaw assembly is configured to receive only a single surgical clip at a time, and the pair of jaws is adapted to receive a surgical clip exteriorly of the jaw assembly.

2. The jaw assembly recited in claim 1, wherein:
the jaws, the support arms, and the bridge are integral and form a jaw component.

3. The jaw assembly recited in claim 2, wherein the housing the molded over the bridge of the jaw component.

4. The jaw assembly recited in claim 1, wherein the support arms are resilient between the open state of the jaws and the closed state of the jaws.

5. The jaw assembly recited in claim 4, wherein at least one of the support arms is biased to maintain the jaws in the open state.

6. The jaw assembly recited in claim 1 wherein:
the support arms are disposed generally in a plane separating a first side of the support arms from a second side of the support arms; and
the housing is disposed with first portions adjacent the first side of the support arms and second portions adjacent the second side of the support arms.

7. The jaw assembly recited in claim 6, wherein the second portions of the housing are connected to the coupling.

8. The jaw assembly recited in claim 6, wherein the jaws are movable in the plane between the open state and the closed state.

9. The jaw assembly recited in claim 8, wherein the support arms are in contact with only the first portions of the housing and the second portions of the housing when the jaws are in the closed state.

10. The jaw assembly recited in claim 1, wherein the first mounting aperture is configured to receive a mounting stub on a multiple-clip cartridge such that the handle assembly can be used with a multiple-clip cartridge.

11. The jaw assembly recited in claim 1, wherein the housing has a proximal end and a distal end, the distal end of the housing comprising an opening, and wherein the support arms and bridge are positioned within the housing such that the support arms extend through the opening in the distal end of the housing, and the bridge is housed by the housing adjacent the proximal end.

12. The jaw assembly recited in claim 1, wherein no surgical clips are received into the housing.

13. The jaw assembly recited in claim 1, wherein the housing has a proximal end and a distal end and an axis extending from the proximal end to the distal end, and wherein the coupling protrudes from the housing in a direction transverse to the axis.

14. The jaw assembly recited in claim 1, wherein the at least one handle comprises a pair of handles and the handle assembly further comprises a pair of control arms pivotally coupled about a hinge forming the scissor configuration and wherein in an operative disposition, the control arms of the handle assembly are disposed adjacent the support arms.

* * * * *